(12) United States Patent
de Jonge

(10) Patent No.: US 7,992,430 B2
(45) Date of Patent: Aug. 9, 2011

(54) SAMPLING DEVICE AND METHOD FOR MONITORING OF LIQUIDS

(75) Inventor: Hubert de Jonge, Viborg (DK)

(73) Assignee: Sorbisense Aps (DK)

( * ) Notice: Subject to any disclaimer, the term of this patent is extended or adjusted under 35 U.S.C. 154(b) by 584 days.

(21) Appl. No.: 12/088,619

(22) PCT Filed: Sep. 28, 2005

(86) PCT No.: PCT/DK2005/000613
§ 371 (c)(1),
(2), (4) Date: May 8, 2008

(87) PCT Pub. No.: WO2007/036226
PCT Pub. Date: Apr. 5, 2007

(65) Prior Publication Data
US 2008/0236257 A1    Oct. 2, 2008

(51) Int. Cl.
*G01N 1/10* (2006.01)
(52) U.S. Cl. .................................................. 73/61.59
(58) Field of Classification Search .............. 73/61.41, 73/61.43, 61.56, 61.59
See application file for complete search history.

(56) References Cited

U.S. PATENT DOCUMENTS

| 3,377,868 A | 4/1968 | Dowling et al. |
| 5,777,214 A * | 7/1998 | Thompson et al. ........... 73/61.59 |
| 6,706,094 B2 * | 3/2004 | Browne ......................... 95/241 |
| 2008/0011061 A1 * | 1/2008 | Sihalla ........................ 73/64.56 |

FOREIGN PATENT DOCUMENTS

| GB | 1107180 | 3/1968 |
| JP | 2000275226 A | 10/2000 |
| WO | 03098167 | 11/2003 |

OTHER PUBLICATIONS

J. F. Pankow, et al. "A tube and cartridge method for down-hole sampling for trace organic compounds in ground water". Ground Water, Well Journal Pub. Co. Nov. 1985, p. 775-782, vol. 23, No. 6.
Herbert De Jonge, et al. "A device and method for flux-proportional sampling of mobile solutes in soil and ground water". Environmental Science and Technology 01, Jan. 2005, pp. 274-282, vol. 39, No. 1.
International Search Report PCT/DK2005/000613 Dated May 17, 2006.

\* cited by examiner

*Primary Examiner* — John Fitzgerald
(74) *Attorney, Agent, or Firm* — Cantor Colburn LLP

(57) ABSTRACT

Methods and devices for measuring chemical or biological properties of a liquid from a subsurface position are disclosed, wherein a closed casing is submerged in the liquid to be sampled. The flow of the liquid for the sampling is driven by a hydrostatic pressure and is thus independent of pumps or the like when placed at the correct subsurface position. The flow rate is in a first aspect of the present invention controlled by providing a constant hydrostatic pressure during the sampling period. Alternatively, the inlet is provided with a cartridge comprising a tracer material, which is partly soluble by the liquid and is released proportional to the flow rate.

37 Claims, 5 Drawing Sheets

SAMPLING DEVICE AND METHOD FOR MONITORING OF LIQUIDS

TECHNICAL FIELD OF THE INVENTION

The present invention relates to methods and devices for measuring chemical or biological properties of a liquid from a subsurface position.

BRIEF DISCUSSION OF RELATED ART

The most frequently used method to take liquid samples from, for example, natural water bodies including groundwater, rivers and lakes is by pumping a certain volume of the liquid into a closed casing. In a groundwater well for example, the common method is to sink a pump into the groundwater well and pump the groundwater through tubing to a sample container on the surface.

To avoid pumping, so called no-purge samplers have been developed that sample the water down-hole in the well, thus avoiding the need for actively pumping the water to the surface, for example a device as disclosed in U.S. Pat. No. 6,481,300. A low-flow sampling well insert is disclosed in WO 2003/072908 (Learned), in which the flow into a sample tube is allowed after exerting downward pressure on the sample tube. A disadvantage of this method is that due to the slow rate of sampling, volatile compounds that enter the sampling tube, can volatilize and be removed again from the sampling tube through the air-outlet.

In a lake or the sea it is also possible to use a method in which the sample casing is lowered to a certain depth and instantaneously filled upon actuators (electronic or other) that allows entrance of the surrounding water to the casing (e.g. U.S. Pat. No. 3,367,191 Richard). Variations maybe several sampling casings at several depths that are opened simultaneously (e.g. EP 1 521 954, Sauter). After the collection of these so called grab samples, the casing is usually stored refrigerated and brought to the laboratory for subsequent analysis of chemical properties and concentration of solutes. Often measured parameters measured in the laboratory are plant nutrients, especially nitrogen and phosphorus, heavy metals, pesticides, and other organic contaminants.

An important limitation of above described methods is that the obtained results represent a concentration value at a fixed period in time. Concentrations of chemicals in water do often vary strongly in time. In order to have a representative average concentration over a longer period, e.g. months up to one year, it is necessary to obtain several samples during this period, which is expensive and time consuming because it requires repeated site visits and chemical analyses.

Another problem encountered by the above described methods is that for many chemical parameters it is necessary to refrigerate the obtained water samples for conservation purposes before it is analyzed in the laboratory. Hence, the sample container must be shipped under refrigerated conditions and the chemical analysis must be performed soon after the sampling event. Further, it cannot be avoided that the liquid and dissolved chemicals come into physical contact with equipment such as tubing and sample container. Therefore it is of importance that these materials are chosen such that they do not interfere with or adsorb the compounds to be measured. Also, these materials do have to be very clean to avoid false positive detects, which is especially important for micro-contaminants that are detected at very low concentration levels. Hence, either disposable equipment—e.g. tubing, flasks—are used, or the sample containers have to be cleaned very thoroughly in between two samplings. This cleaning process is time- and energy consuming and also requires the frequent use of organic solvents.

One way to obtain time-resolved information is by using automated samplers that takes a series of samples in time, usually by means of a pump that is time-controlled by an electronic device. This pump transfers the liquid in response to a sensor or following pre-programmed time intervals into a series of containers, and thereby collects a series of samples without the user being physically being present at the location (see e.g. DE 198 36 292). The water samples can either be analyzed separately, or they can be mixed such that time-averaged concentrations can be obtained. However, the conservation problem of the water sample is still applicable; hence the water samples device should preferably be refrigerated when taking samples over longer time periods. As a consequence, these devices are power-consuming and repetitive site visits need to be performed to change battery power supply or the like, so they are less suited for remote locations.

In WO 98/40717 (Fiedler and Davison) is disclosed an improved automated sampler, where the pump is used to transfer water at a controlled rate through a collecting cartridge which is filled with an adsorbent that is selected to adsorb the solutes of interest, a so called solid phase extraction cartridge. After the device is installed for a certain amount of time, the cartridges are brought to the laboratory, and adsorbed solutes are extracted from the adsorbent and measured using standard methods. Because the pump is working at a controlled flow rate, it is also possible to know the amount of water passing the cartridge, and, hence, backward calculate the average solute concentration during the sampling period. A similar apparatus for time-averaged sampling of chemicals in groundwater is disclosed in U.S. Pat. No. 4,717,473 (Scott and Russel), in which the pumping unit and sorptive media cartridge are installed down-hole in a groundwater well. This method is called on site solid phase extraction, the primary advantage being that it eliminates the need for the storage of aqueous samples. However, these devices still have power consuming pumps and other electronic functions, making the sampler expensive and susceptible to servicing.

In WO 03/098167 (de Jonge and Rothenberg) and WO 01/33173 there are disclosed passive sampling devices that are placed in moving liquids to estimated the flux of the liquid and dissolved solutes. Described are application in, among other, groundwater and aquifers. These devices consist of porous liquid-permeable units that are in capillary contact with the surrounding liquid. The permeable units contain adsorbents that capture the solids of interest, and tracer compounds that are leached out of the units in proportion with the volume of the liquid passing the sampler. The technical procedure involves installation of the device in the medium of interest, allowing passive capillary contact with the surrounding liquid over a certain time period, removing of the device, and retrieving the accumulated amount of the solute and the remaining amount of the tracer compound. The advantage is that these devices are able to measure both an in-situ flux (mass and momentum movement) of the solute and the liquid as well as an average concentration (mass per volume) as opposed to above described methods that only measure solute concentrations. Also, these devices do not have power consuming functions and therefore do not need to be serviced when installed for longer periods at remote locations. These methods have the disadvantage, that the optimal length of the installation period is dependent on the magnitude of the fluid momentum flux adjacent to the sampler: the lower the flux, the longer it takes to do an accurate flux measurement. Clearly, the magnitude of the flux is normally not known a-priori, as the objective of the device is to measure the actual flux. Another disadvantage is that these devices are not suited for applications in open water bodies such as lakes, marine environments, and ponds, as the flow in these environments is either too high, turbulent, or too low to be accurately measured. As these devices depend on a laminar flow conditions, they can in this case measure neither solute flux nor solute concentrations.

Another passive sampling method used a tube and cartridge with sorptive media directly installed in a groundwater well (Pankow et al., Ground Water, Vol. 23, no. 6, 1985). The cartridge was connected with the tubing and a flow restrictor, the tubing leading to the surface, and the cartridge lowered down the well; the water column pressed the water through the cartridge containing a sorptive media. The main disadvantage from this method is that the flow rate of sampling is not constant over time, due to the rising water column in the tube, causing a gradual increase in the back pressure and therewith a decrease in the sampling flow rate. Therefore, the method is less suited to obtain time-averaged concentrations.

Other documents disclose passive samplers, in which the mass transfer from the surrounding liquid to the collector occurs through a membrane that is impermeable to the sampled liquid but permeable to the investigated solutes (U.S. Pat. No. 5,996,423, WO 92/04646, U.S. Pat. No. 5,904,743, WO 01/14852). Mass transfer through the semi-permeable membrane is then governed by diffusion, and the mass concentration of the solute in the surrounding liquid is calculated using either equilibrium values or diffusion parameters. An important feature of the method is that it measures only the free-dissolved phase, and is therefore often used as a measure for the bio-available fraction. Also, the method these devices can in principle sample solutes over longer time periods. One disadvantage of this method is that the concentration of the solute in the fluid medium directly adjacent to membrane is dependent on the mixing of the liquid, and hence on the turbulence and/or flow rate surrounding the membrane (Gustavson, K. E.; Harkin J. M., Environ. Sci. Technol. 2000, 34, 4445-4451). In the absence of sufficient mixing, the mass transfer through the membrane will be controlled by the magnitude of the liquid flux in the surrounding fluid medium, and a direct back-calculation of the concentration with diffusion parameters is no longer possible. Another disadvantage is that diffusion coefficient for each single monitored molecule should be calibrated individually (Huckins et al., Environ. Sci. Technol. 1999, 33, 3918-3923). Diffusion parameters can be strongly sensitive to temperature changes. Another disadvantage is that these devices are not permeable to mobile colloids, that can act of carrier of strongly sorbed compounds such as phosphorus, heavy metals, apolar contaminants etc. Hence, solutes that are sorbed to suspended colloids are not sampled using these devices.

Thus, the overall problem to be solved with the known devices is to provide a method for in-situ sampling of high-precision average chemical or biological properties of a stagnant or flowing liquid over a longer time period without the need for pumping, vacuum or other power consuming functions as well as a device therefore.

This and other problems are solved with the present invention as described in the claims and in the description below.

BRIEF SUMMARY OF THE INVENTION

The method and device of the present invention comprises a closed casing submerged in the liquid to be sampled, wherein the above object is reached and a high precision of average properties is obtained. The flow of the liquid for the sampling is driven by a hydrostatic pressure and is thus independent of pumps or the like when placed at the correct subsurface position, and the flow rate is in a first aspect of the present invention controlled by providing a liquid conduit from the inlet for the liquid into the casing and to a position inside the cavity of the casing well above the bottom of the cavity, so that the hydrostatic pressure and thus the flow rate is substantially constant during the sampling period. Alternatively, the inlet is provided with a cartridge comprising a tracer material, which is partly soluble by the liquid and is released proportional to the flow rate. Thus, when the device is analyzed after the sampling period, an analysis of the remaining tracer material in the cartridge will reveal the total flow of the liquid that has flown into the cavity of the casing. The sampling may take place over a long period, from days to months, and the amount of liquid within the cavity at the end of the sampling period is less than the total flow due to evaporation. Furthermore, the two methods, i.e. the liquid conduit and the tracer material may be combined to provide a high degree of precision of the average values obtained.

Thus, the present invention relates to a method for determining chemical or biological properties of a liquid and a device therefore, the method comprising the steps of situating a sampling device having a fluid-filled cavity at a subsurface position below the upper surface of the liquid, the fluid having a density lower than the liquid, allowing a flow of the liquid through an inlet opening of the sampling device and into the cavity for a sampling period, simultaneous allowing a flow of the fluid out from the cavity through an outlet opening of the sampling device, removing the sampling device from the subsurface position for subsequent analysis for determining said chemical or biological properties of the liquid, wherein the inlet opening of the sampling device is connected to a liquid conduit having its outlet inside the cavity and above the bottom of the cavity, so that the free surface of the liquid inside the cavity during most of the sampling period, such as at least 80% thereof, preferably at least 95% thereof, is below the liquid conduit outlet, for the hydrostatic pressure driving the flow of the liquid into the cavity to be substantially constant during most of the sampling period.

The fluid in the cavity at the beginning of the sampling period will normally be atmospheric air, but may e.g. for sampling in other liquids than water, such as oil, be a lighter liquid, such as an alcohol.

Said sampling period is preferably at least one hour, preferably within the range of 1 day to 400 days and more preferred within the range of 14 days to 200 days. For the design of the device, the volume inside the cavity below the level of the liquid conduit outlet and the liquid inflow rate may be chosen so as to allow for such sampling period.

The liquid inflow rate is in a preferred embodiment of the present invention within the range of 0.0001-5 Litres/day, more preferred within 0.0005-0.1 Litres/day and even more preferably within 0.001-0.02 Litres/day. In order to control the liquid inflow rate, the inlet of the sampling device may be provided with a backpressure regulating device so as to regulate the liquid inflow rate. In a preferred embodiment, the backpressure regulating device comprises a capillary tubing having an internal diameter of 10-2000 µm, preferably 10-500 µm and more preferably 25-150 µm, and the capillary tubing may constitute at least a part of the liquid conduit.

Alternatively, the backpressure regulating device may be constituted by an inlet filter having a nominal filtration porosity of 0.1-2000 µm, preferably 0.5-100 µm, and more preferably 1-20 µm or an in-line back-pressure regulating restriction valve.

The chemical or biological properties of the sampled liquid may be determined from analysis of the content of the cavity. However, this is not expedient for all types of properties, as the components in the liquid in the cavity may deteriorate over time, e.g. due to evaporation and/or the exposure to atmospheric air. Thus, it may be advantageous that the inflow passes through a cartridge containing a material that interacts with components of the liquid, and said chemical or biological properties of the liquid are determined by a subsequent analysis of the cartridge.

In particular, the cartridge may contain at least one sorbent matrix being permeable to and insoluble by the liquid, the matrix comprising a material having sorbent properties for components of the liquid being indicative for the chemical or biological properties thereof to be determined. The material may be an organic, inorganic or hybrid organic/inorganic material. In a preferred embodiment, the sorbent matrix is chosen from the following groups of materials: silica, aluminium silicate, aluminium zirconium, metal oxides, synthetic ion exchange resins, carbonaceous materials, zeolites, carbohydrates and synthetic polymeric materials.

The cartridge may further as mentioned previously comprise at least one fluid permeable partially soluble tracer material, which is released with controlled rate from the cartridge into fluids to be measured, so that the total flow trough the cartridge may be determined from analysis of the cartridge. Details about preferred embodiments of the application of the tracer material are discussed further below.

In a particular embodiment, the device is equipped with more than one such cartridge containing identical and/or different sorbent matrices and/or tracer substances.

The present invention relates in the alternative aspect to a method for determining chemical or biological properties of a liquid and a device therefore, the method comprising the steps of
situating a sampling device having a fluid-filled cavity at a subsurface position below the upper surface of the liquid, the fluid having a density lower than the liquid,
allowing a flow of the liquid through an inlet opening of the sampling device and into the cavity for a sampling period,
simultaneous allowing a flow of the fluid out from the cavity through an outlet opening of the sampling device,
removing the sampling device from the subsurface position for subsequent analysis for determining said chemical or biological properties of the liquid,
wherein the inflow passes through a cartridge containing at least one liquid permeable partially soluble tracer material, which is released with controlled rate from the cartridge into fluids to be measured, and a measure for the total liquid flow through the cartridge is obtained by analysing the remaining content of tracer material in the cartridge.

The at least one tracer material is in a preferred embodiment chosen from the following groups of materials: inorganic, organic and hybrid organic/inorganic salts; organic, inorganic or hybrid organic/inorganic solids, including polymers, copolymers, block copolymers and oligomers in which hydrolysis of certain bonds can lead to the loss of part of the material; and microencapsulated materials.

The tracer material may in particular be a salt having a solubility product ($K_{sp}$) in the fluid in question of between $10^{-2}$ and $10^{-60}$, preferably between $10^{-2}$ and $10^{-40}$ and more preferably between $10^{-5}$ and $10^{-12}$.

The tracer material is preferably chosen from the following group of salts: $CaF_2$, Ca-Citrate, $CaHPO_4$, Ca-oleate and Ca-laurate, which salts have suitable properties for the purpose.

Furthermore, the cartridge may further contain a material that interacts with components of the liquid, and said chemical or biological properties of the liquid are determined by analysis of the cartridge, in particular at least one sorbent matrix being permeable to and insoluble by the liquid, the matrix comprising a material having sorbent properties for components of the liquid being indicative for the chemical or biological properties thereof to be determined. The sorbent matrix may be made from an organic, inorganic or hybrid organic/inorganic material.

In particular, the sorbent matrix may be chosen from the following groups of materials: silica, aluminium silicate, aluminium zirconium, metal oxides, synthetic ion exchange resins, carbonaceous materials, zeolites, carbohydrates and synthetic polymeric materials.

In order to provide a constant inflow of the liquid to the cavity, the inlet opening of the sampling device may be connected to a liquid conduit having its outlet inside the cavity above the bottom of the cavity, so that the free surface of the liquid inside the cavity during most of the sampling period is below the liquid conduit outlet for the hydrostatic pressure driving the flow of the liquid into the cavity to be substantially constant during most of the sampling period. The preferred features of such liquid conduit and the possible provision of a backpressure regulating device are discussed previously.

Said sampling period is preferably at least one hour, preferably within the range of 1 day to 400 days and more preferred within the range of 14 days to 200 days. For the design of the device, the volume inside the cavity below the level of the liquid conduit outlet and the liquid inflow rate may be chosen so as to allow for such sampling period.

The liquid inflow rate is in a preferred embodiment of the present invention within the range of 0.0001-5 Litres/day, more preferred within 0.0005-0.1 Litres/day and even more preferably within 0.001-0.02 Litres/day. In order to control the liquid inflow rate, the inlet of the sampling device may be provided with a backpressure regulating device so as to regulate the liquid inflow rate. In a preferred embodiment, the backpressure regulating device comprises a capillary tubing having an internal diameter of 10-2000 µm, preferably 10-500 µm and more preferably 25-150 µm, and the capillary tubing may constitute at least a part of the liquid conduit.

Alternatively, the backpressure regulating device may be constituted by an inlet filter having a nominal filtration porosity of 0.1-2000 µm, preferably 0.5-100 µm, and more preferably 1-20 µm or an in-line back-pressure regulating restriction valve.

BRIEF DESCRIPTION OF THE DRAWINGS

Examples of the present invention are illustrated with the enclosed drawings, of which

Figure 1:
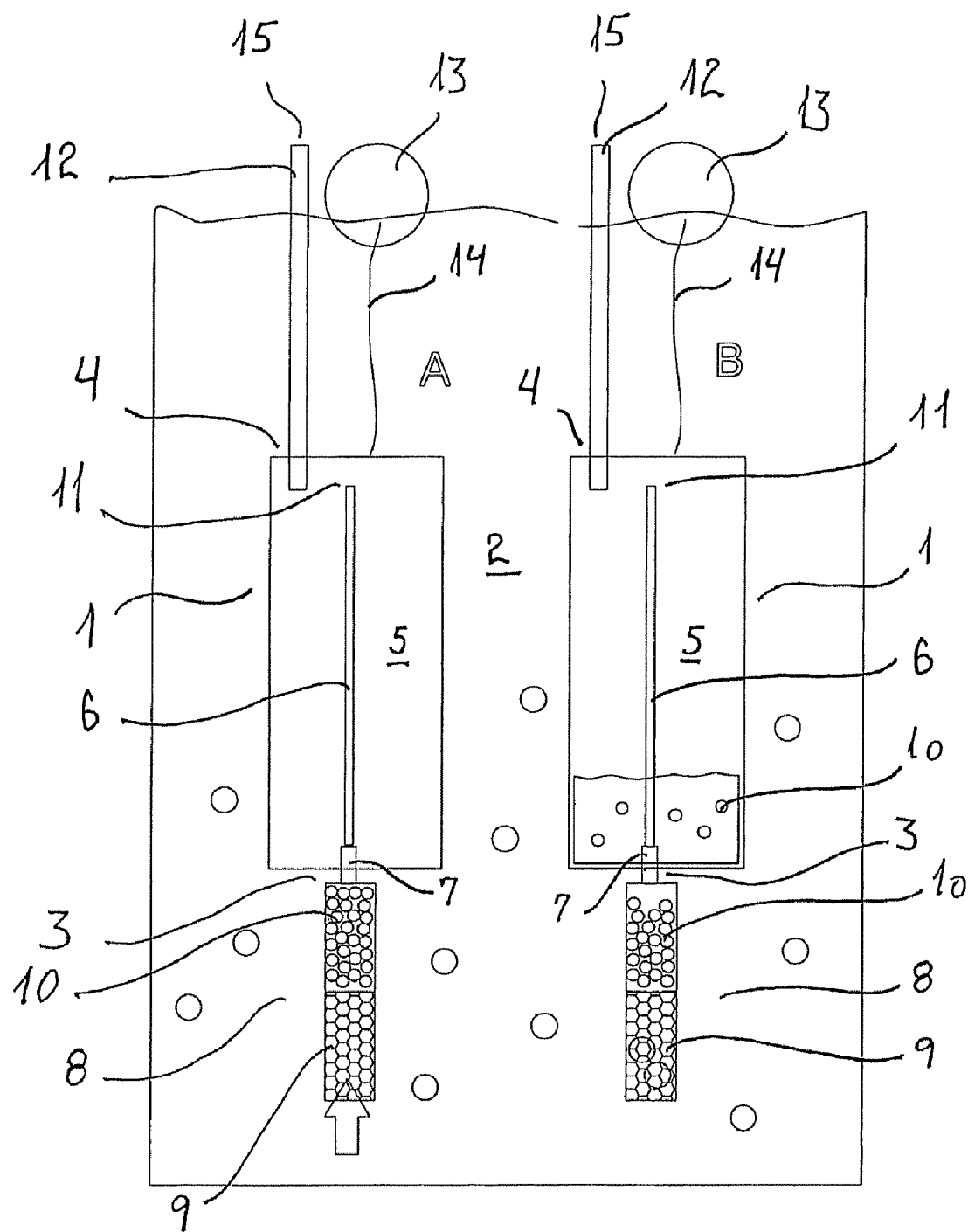
FIG. 1 shows a first embodiment of a device according to the present invention installed at a subsurface position prior to operation (FIG. 1A) and during operation (FIG. 1B) of the device.

The drawings are enclosed for describing preferred embodiments of the present invention and are not to be regarded as limiting for the scope of protection as outlined in the claims.

DETAILED DESCRIPTION OF THE INVENTION

In the figures are shown improved sampling device and methods in accordance with the present invention for in-situ monitoring of continuously time-averaged concentration values of solutes over longer time periods, say from one day up to a year.

FIG. 1A shows a schematic view of one preferred embodiment of the invention, having a casing 1 of the device submerged in the liquid 2 upon installation. The casing 1 itself may have any desirable shape, but often a cylindrical shape will be preferred. The casing 1 may be produced of any desirable material that is water-tight and can withstand the pressure of the surrounding liquid 2, including but not limited to stainless steel, polyethylene, polypropylene, polytetrafluorethylene, polyoxmethylene, and polyvinyl chloride. Also, the casing 1 itself can be assembled from several components (not shown in figure). As an example, a cylinder may be capped with a top and bottom lid, secured to the cylinder through water tight fittings, e.g., using flexible o-rings. The top and bottom lid contain the inlet 3 and outlet conduits 4. Depending on the volume weight of the casing material, the wall thickness of the casing may be chosen such that weight of the casing is higher than the weight of the liquid 2 displaced by the casing. Alternatively, if the casing is buoyant in the liquid, it is possible to attach a weight to the casing (not shown). In both cases, the casing can be installed through a flexible wire at a certain depth without the need of securing the sampler to a fixed point.

The interior cavity 5 of the casing 1 is initially filled with atmospheric air and is in capillary contact with the exterior liquid 2 through a capillary tubing 6, inlet conduit 7, and solid phase extraction cartridge 8. The mode of fitting of the capillary tubing 6 and cartridge 8 to the casing 1 and inlet conduit 7 can be any preferred water-tight fitting. Examples of this fitting include, but are not limited to, a luer, luer-lock, flat bottom fitted fittings with tight fitting o-rings, and threaded fittings with expandable ferrules. The solid phase extraction cartridge 8 contains at least one adsorbent 9. This adsorbent or mix of adsorbents is selected with the view of adsorbing a certain range of solutes, as described in more detail in WO 03/098167. The use of a cartridge 8 with a sorbent media 9 at the inlet conduit is especially needed if constituents are to be sampled that should not be exposed to air, either because of a risk of volatilization from the casing 1, or because of a risk of chemical or microbiological degradation. The sorption of the constituents is very strong so that the compounds are chemically and biologically preserved during the sampling period.

The cartridge depicted in FIG. 1 also contains at least one tracer substance 10 that has the function of recording the volume of the water passing the cartridge. The tracer substance 10 goes into solution in proportion to the volume passing the cartridge 8, as described in detail in WO 03/098167. The adsorbent 9 and tracer substances 10 are kept in place with the help of porous filters, called frits (not shown in FIG. 1).

Such frits may be produced by any suitable material, including but not limited to porous glass, porous plastic (such as polyethylene, polytetrafluorethylene, or polyetheretherketon), porous metals (such as steel or titanium) or metal alloys. Besides having the function of keeping the adsorbent 9 and tracer materials 10 physically secured in the cartridge 8, the frits also physically precludes particles larger than the nominal pore size of the frit to enter the cartridge 8.

An inline filter positioned in between the cartridge 8 and the capillary tubing 6 can be used in order to prevent small particles to enter and possibly block the capillary tubing 6. The capillary tubing 6 has the function of controlling the hydraulic resistance of the liquid path into the cavity 5 of the casing 1. Capillary flow theory learns that, given a certain pressure head, the flow is proportional with $r^4$, with r is the internal radius of the capillary tubing, and proportional with $1/L$, with L is the length of the capillary tubing 6. Hence, the radius and length of the capillary tubing 6 can be used to control the flow rate of the liquid into the cavity 5 of the casing 1. In FIG. 1, the capillary tubing 6 is extended vertically into the casing 1, and has its outlet 11 near the top of the sample casing 1, so the direction of the liquid 2 entering the casing 1 is upward. In order to reach a desired length and hydraulic resistance of the capillary tubing 6, it is also possible to couple two or more capillaries with different diameters in series.

The cavity 5 in the interior of casing 1 in FIG. 1 is also equipped with a air venting conduit 12, the function of which is to equalize the pressure within the casing with the atmospheric pressure above the sampled liquid.

Upon installation of the preferred embodiment depicted in FIG. 1, there is a hydraulic pressure gradient between the inlet of the solid phase extraction cartridge 8, caused by the weight of the liquid column above the inlet and hereafter referred to as the head pressure, and the cavity 5 at the interior of the casing 1, being in equilibrium with atmospheric pressure through air venting conduit 12 extending upwards above the upper surface of the liquid 2. The cartridge 8 and the capillary tubing 6 will fill with the liquid 2 and the liquid 2 will enter the cavity 5 interior of the casing 1. Until the cartridge 8 and capillary tubing 6 are completely filled, there is a slight build up of backpressure since the liquid 2 flows upward and the increasing weight of the water column in the cartridge 8 and the capillary tubing 6 contributes to the increasing back pressure. To minimize the effect, the cartridge 8 can be pre-wetted before securing the cartridge 8 to the inlet conduit 7 and installing the sampler. The volume of the interior of the capillary tubing 6 is very small, typically less then 0.1 ml, in comparison to the interior volume of the cavity 5 of the casing 1, which is typically larger than 100 ml, such as between 200 ml and 3 liters. Hence, the varying back pressure only affects less than 0.1% of the sampled volume when the cartridge 8 is pre-wetted. When the cartridge 8 and capillary tubing 6 are completely filled, the cavity 5 of the casing 1 is filled in proportion to the pressure head above the sampler (FIG. 1B). As this device is attached to a floating member 13 by means of a flexible wire 14, the entire sampling unit will be hanging in the liquid 2 at constant depth, even if the free liquid surface level is fluctuating.

Hence, the sampling rate of the liquid entering the casing will be substantially constant in time until the liquid level in the casing reaches the level of the outlet 11 of the capillary tubing 6. The preferred installation time is usually known beforehand, and for those skilled in the art it will be possible to design a preferential combination of internal casing volume, capillary tubing 6 length and diameter, the parameters that combined determine the optimal fluid sampling rate. From the above description it is clear that this preferential combination will be different depending on the depth of installation. In addition, this preferential combination will depend on the viscosity of the sampled liquid 2, and therefore to a certain degree also on the temperature of the adjacent liquid.

The mode of operation of the device as shown in FIG. 1, once assembled towards beforehand known criteria, depth of installation and required installation time, is very easy. The sampler is installed at known depth; the sampler is passively filled at a predetermined rate, after which the sampler is removed. The installation time will vary according to the aim of the sampling and may vary from, for example, one day up to several months. After removal of the sampler, the cartridge and the sampled fluid are analyzed for chemical or biological properties. The analysis of the cartridge 8 is described in detail in WO 03/098167. Briefly, the adsorbent 9 is extracted and analyzed for the mass of chemical or biological compounds sorbed, and the cartridge 8 is analyzed for the displaced amount of tracer substance 10. The liquid sampled in the cavity 5 of the casing 1 may also be analyzed, both with respect to the quantity (volume) and to the chemical constituents so as to derive information on the chemical and/or biological concentrations of the sampled liquid.

According to other preferred embodiments of the invention, not shown in FIG. 1, more than one cartridge 8 may be fitted to the casing 1, These cartridges 8 may have similar adsorbents 9 and tracer compounds 10, in order to quantify the precision and reproducibility of the sampling method. Alternatively, these different cartridges 8 may be equipped with different adsorbent types 9 and/or tracer compounds 10 or different amounts of tracer compounds 10. This is done to sample a wider range of chemical or biological parameters.

According to another preferred embodiments of the invention, not shown in FIG. 1, the cartridge 8 or cartridges 8 may be arranged on the top part of the casing 1, so that the flow of the liquid 2 through the capillary tubing 6 is downward rather than upward. The benefit of this position is that it is possible to sample the liquid 2 closer to the liquid surface. The position of the cartridges 8 shown in FIG. 1 prevents larger particles to settle on the inlet of the cartridge 8, which is a benefit when the liquid 2 contains high loads of suspended particles. According to another preferred embodiments of the invention, not shown in FIG. 1, the cartridge 8 or cartridges 8 may be positioned horizontally on the vertical walls of the casing 1. This may be of advantage when the device is installed in shallow liquids, or when for other reasons it is considered important that there is no vertical flow through the cartridge 8, adding to the overall pressure gradient of the flow through the cartridge 8.

Figure 2:
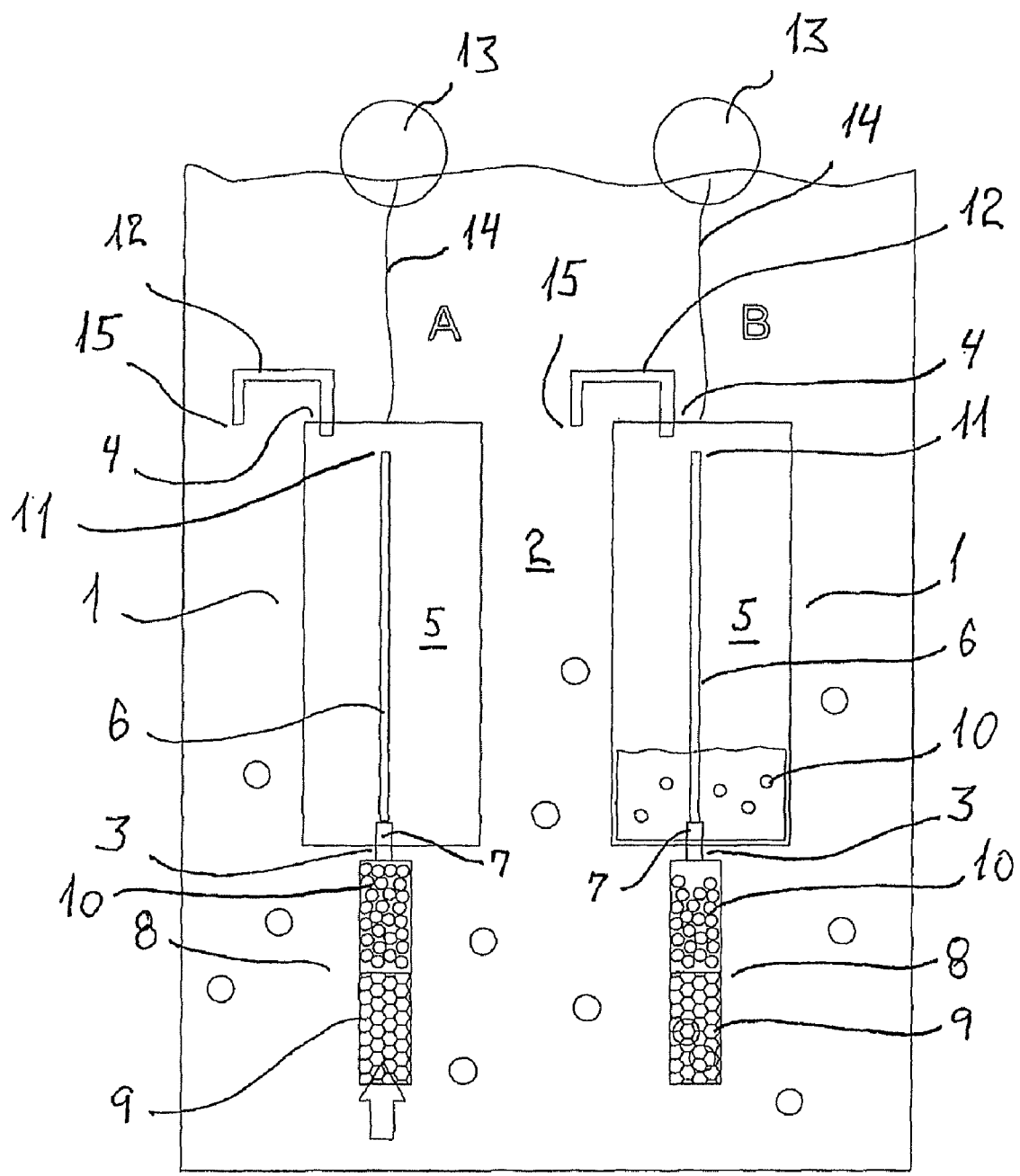
FIG. 2 shows a second embodiment of a device according to the present invention installed at a subsurface position prior to operation (FIG. 1A) and during operation (FIG. 1B) of the device.

FIG. 2 shows another preferred embodiment of the sampling device, different from the one of FIG. 1 in that the internal pressure in the cavity 5 of the casing 1 is regulated by the air venting conduit 12 which has an outlet 15 below the surface of the liquid 2 to obtain a hydrostatic pressure between the outlet 15 and the outlet 11 of the capillary tubing 6 independent from the depth of the sampling device. This outlet 15 from the cavity 5 reduces the pressure gradient over the inlet of the sampler. When the sampler depicted in FIG. 2 is submerged in a liquid 2 and the capillary tubing 6 is filled with the liquid 2, the pressure gradient driving force that regulates the flow into the cavity 5 of the casing 1 is proportional to the head of the liquid 2 above the outlet 11 of the capillary tubing 6, positioned in the top section of the cavity 5 of the casing 1, minus the head of the liquid above the outlet of the air-filled conduit 12. Hence, this pressure gradient is constant through the sampling period and independent of the depth of installation with respect to the level of the liquid 2. Air will be displaced from the cavity 5 through the outlet 15 while the cavity 5 is slowly filled at a constant rate defined by the above described constant pressure gradient. The pressure gradient in FIG. 2 can be largely reduced compared to FIG. 1, and therefore wider capillary tubing 5 and/or coarser entrance filters with less hydraulic resistance may be used. For those skilled in the art it will be possible to find a preferred combination of filter porosity, capillary length and diameter, to design the optimal fluid sampling rate for a given volume of the cavity 5 and desired installation time for the device. The mode of operation of the device shown in FIG. 2 is essentially the same as above described for the device shown in FIG. 1.

Figure 3:
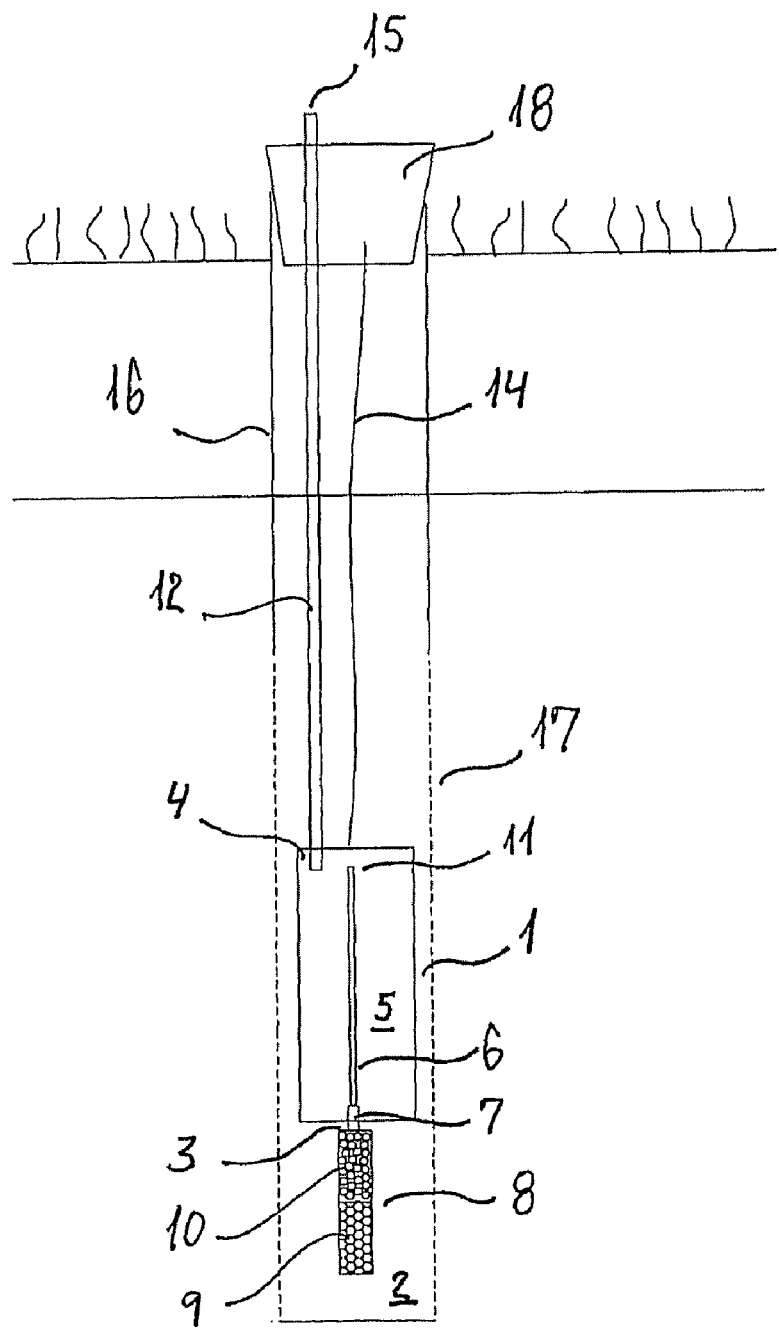
FIG. 3 shows the installation of the sampling device of FIG. 1 in a groundwater well, FIG. 4. is a curve showing the linear relationship of sampling flow rate with depth in the 1-6 m depth interval, and FIG. 5. is a curve showing the linear relationship of sampling flow rate with depth in the 0.4-1.7 m depth interval.

FIG. 3 shows a preferred mode of installation of the sampling device of FIG. 1 in a groundwater well. Such wells are used for drinking water production and for environmental purposes. The well is composed of a solid pipe section 16, the riser pipe, and a slotted section of the pipe 17, also referred to as well screen. The later is in capillary contact with the surrounding groundwater through narrow slots. The whole, or part of, the well screen 17 is either permanently or intermittently below the groundwater table. If the top of the well screen 17 is below the capillary fringe, the water in the pipe rises until the level in the pipe is in equilibrium with atmospheric pressure. In a non-confined aquifer, the surrounding groundwater is also in equilibrium with atmospheric pressure. Hence, in this case the level in the standing pipe and the groundwater level will coincide. The water in the well screen 17 is continuously replenished due to groundwater flow in the surrounding sediment, while the water above the well screen 17 is stagnant and not replenished. The sampler is installed through a flexible wire 14 to the top of the well pipe 16 by means of, for example, a stopper 18. The sampler is installed such that the inlet of the cartridge 8 is level with the slotted section 17 of the pipe, so that the sampler is filled with freshly replenished groundwater. Because the sampler here is fixed with respect to the ground surface, the flow into the sampling device will fluctuate along with fluctuations in the water level in the pipe. This may be desirable, because the groundwater is, in the absence of nearby surface water, proportional with the horizontal groundwater flux. Hence, in a non-confined aquifer the volume of the water displaced into the sampling device can be used as a measure for the average groundwater level during the installation period. In some cases, the rate of groundwater replenishment in the well is so low, that the water-quality in the well is affected by diffusion of gases through the water in the stand-pipe. Therefore, it may be desirable to isolate the slotted section 17 of the well from the riser pipe 16. For those skilled in the art it will be feasible to isolate these sections by the means of packers, for example as disclosed in U.S. Pat. No. 5,259,450 (Fischer).

One advantage of the methods and devices of the present invention is that there is no need for power consuming functions, so that equipment servicing is not needed in between two sampling events. The methods and devices has further the advantage that it is suitable for sampling of solutes with very different chemical nature, both polar and apolar molecules. A further advantage of the methods and devices is that they are suited for sampling in liquids of very different chemical nature, such as water and aqueous solutions, but also apolar liquids such as oil, and organic solvents. A further advantage of the methods and devices is that they may be applied to sample both free-dissolved and colloidally-bound compounds. Another advantage of the methods and devices is that the use of cartridges containing adsorbent media and tracer compounds can be easily stored before transportation to the laboratory, unlike liquid samples that need conservation and rapid analysis in the laboratory. A further advantage of the methods and devices is that the sampling rate of the solutes is not dependent on the diffusion parameters, and the sampling method is suited for both low, medium, and high-flow environments. Also, an advantage of the methods and devices is that the installation period is not dependent on the magnitude of the flux in the surrounding liquid. It is therefore possible to design an optimal configuration of the device for a certain pre-determined installation time without a-priori knowledge of the flow conditions in which the device needs to be installed.

EXAMPLES

Experiments have been performed to document the feasibility of controlling the sampling flow rate at different using atmospheric pressure compensation as shown in FIG. 1 and capillary inlet conduits 6.

Figure 4:
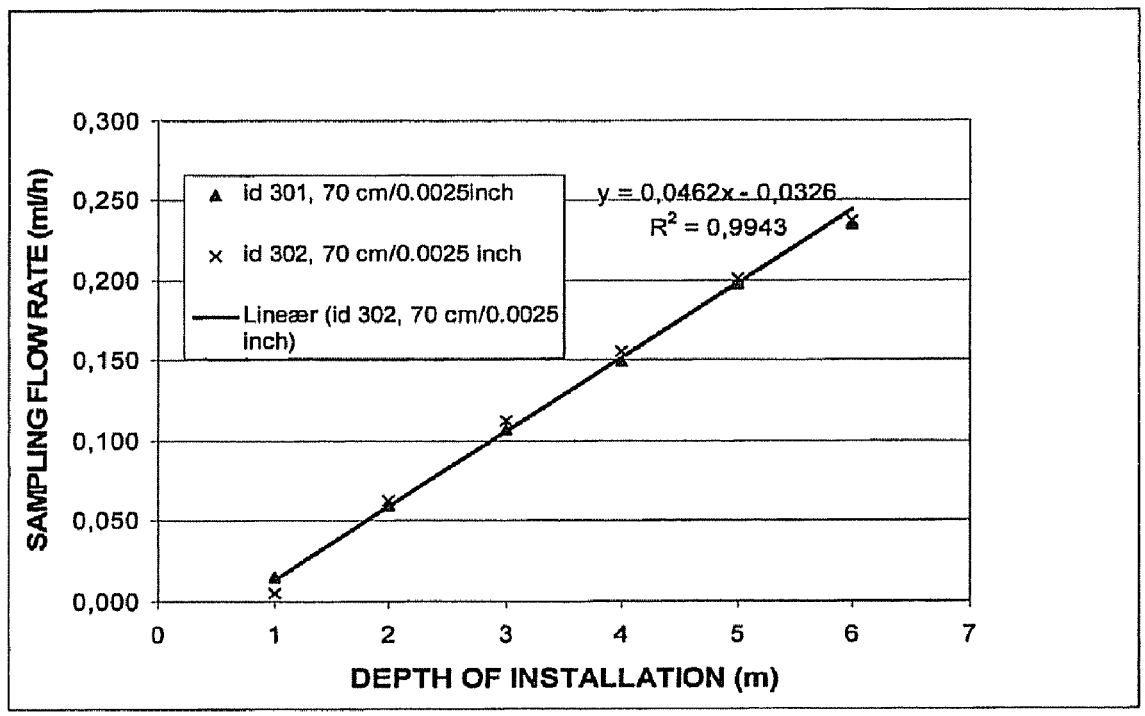

As an example of the sampling flow rate of the sampling method used in shallow groundwater wells (1-7 m depth range), a sampler casing was constructed from a stainless steel cylinder (dimensions 22 mm OD×20 mm ID×105 cm length), and Teflon top and bottom stoppers that were fitted to the cylinder by means of water tight flexible o-rings. The top stopper was constructed with fittings for nylon tubing (dimensions 3.18 mm×1.9 mm×7 m length) and a 7 m flexible steel wire. The bottom stopper was equipped with two external luer fittings and internal threaded fittings. The internal threaded fittings were fitted with a PEEK (polyetheretherketon) capillary (dimensions 1/16 inch×0.0025 inch×70 cm length) extending vertically in the steel cylinder. Two 3 ml plastic cartridge with luer outlets were filled with an ion-exchange resin as a model sorbent and calcium-citrate as a model tracer compound. The resin and tracer were fitted in the cartridge with polyethylene frits with pore size 20 µm. Two cartridges were pre-wetted and fitted to the bottom stopper, and the sampler was lowered in a 7 m standing pipe with 24 mm internal diameter, filled with tap water. The nylon tubing was kept in contact with atmospheric pressure above the standing pipe. In the depth interval 1-7 m the sampler was positioned at six different depths for a fixed period of time, after which the sampler was removed and volume of the accumulated water was determined. Flow rates were measured in the range of 0.01-0.25 ml/hr, depending on the depth of installation, see FIG. 4. The relation of sampling rate with depth is linear with correlation coefficient $R^2$=0.99, which is expected from capillary flow theory.

The effective internal volume of the sampler is approximately 314 ml. With the sampler installed at a depth of 5 m below the water surface, the flow rate would be controlled to have a rate of 0.2 ml/hr, and with one cartridge fitted, the sampler casing would be filled after a period of about 65 days. If a longer installation period is required, either the volume of the casing should be increased, or the capillary dimensions should be changed to reduce the sampling rate.

Figure 5:
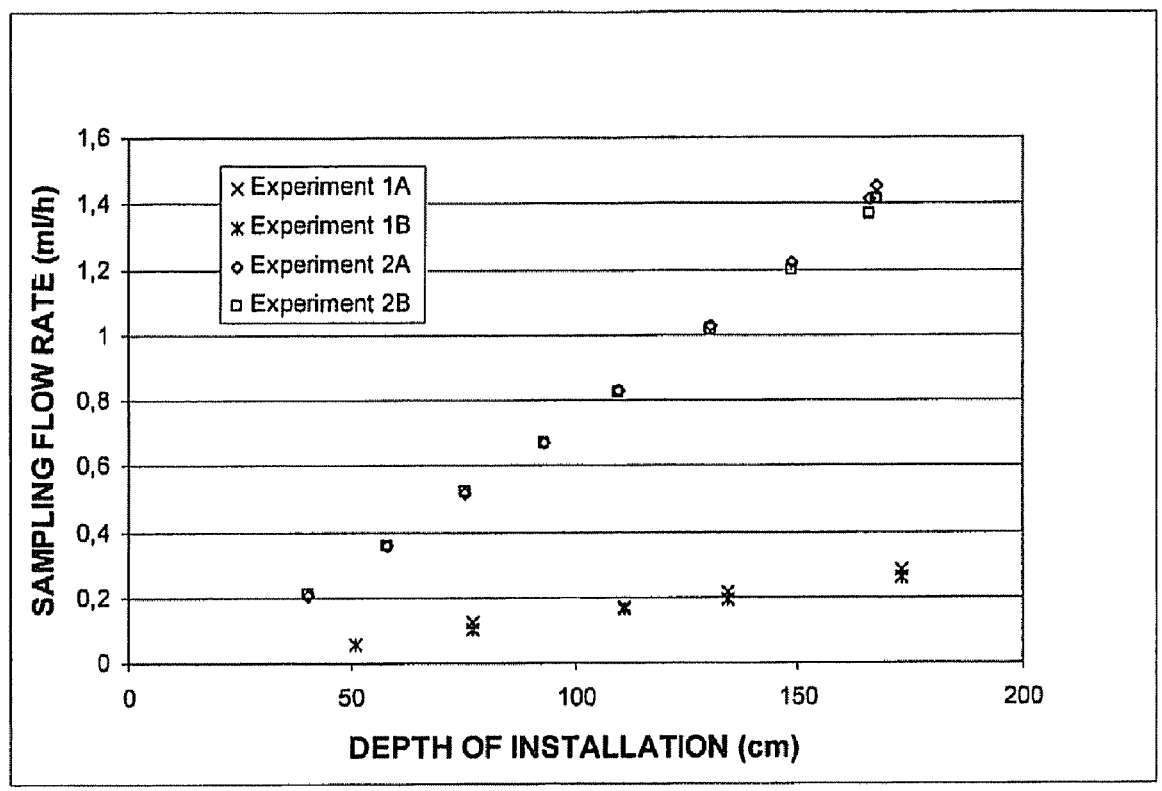

As an example of the sampling method used in shallow surface water (0.3-2 m depth), two standard glass bottles were used as a sampler casings. The bottles were closed with a Teflon lid that was constructed with water-tight fittings for nylon tubing (dimensions 3.18 mm×1.9 mm×2 m length). The lid was further equipped with an external luer fitting and an internal threaded fitting. The internal threaded fitting was for each of the two bottles fitted, in experiment 1, with PEEK capillaries (dimensions 1/16 inch×0.0025 inch×8 cm length), and, in experiment 2, with PEEK capillaries (dimensions 1/16 inch×0.004 inch×8 cm length). Two 3 ml plastic cartridge with luer outlets were packed as described above, pre-wetted, and fitted to the luer fittings. Further, the lid was equipped with the nylon tube extending to the bottom of the glass bottle. The two bottles were lowered in an upside-down position in a water reservoir and mounted on a support. The nylon tube was in equilibrium with the surrounding atmospheric pressure above the reservoir. In the depth interval 0.3-1.7 m the sampler was positioned at five different depths in experiment 1, and at eight different depths in experiment 2, for a fixed period of time. Then the sampler was removed and volume of the accumulated water was determined. In experiment 1, the flow rates were controlled in the range of 0.05-0.25 ml/hr, depending on the depth of installation, see FIG. 5. In experiment 2 with the wider capillaries, the flow rates were controlled in the range of 0.2-1.5 ml/hr, depending on the depth of installation, see FIG. 5. For both capillaries, the relation of sampling rate with depth was linear as expected from capillary flow theory.

The invention claimed is:

1. A method for determining chemical or biological properties of a liquid, comprising:
    situating a sampling device having a fluid-filled cavity at a subsurface position below an upper surface of the liquid, the fluid having a density lower than the liquid,
    allowing a flow of the liquid through a cartridge containing a material that interacts with components of the liquid and into an inlet opening of the sampling device, said inlet opening is provided with a backpressure regulating device so as to regulate a liquid inflow rate into the cavity for a sampling period, said backpressure regulating device comprises a capillary tubing having an internal diameter of 10-500 µm
    simultaneously allowing a flow of the fluid out from the cavity through an outlet opening of the sampling device,
    removing the sampling device from the subsurface position for subsequent analysis for determining said chemical or biological properties of the liquid,
    wherein the inlet opening of the sampling device is connected to a liquid conduit having its outlet inside the cavity and above a bottom of the cavity, so that the free surface of the liquid inside the cavity, during most of the sampling period is below the liquid conduit outlet, for the hydrostatic pressure driving the flow of the liquid into the cavity to be substantially constant during most of the sampling period.

2. A method according to claim 1, wherein the fluid in the cavity is a gas.

3. A method according to claim 1, wherein said sampling period is at least one hour.

4. A method according to claim 1, wherein the liquid inflow rate is within the range of 0.0001-5 Liters/day.

5. A method according to claim 1, wherein said chemical or biological properties of the liquid are determined by analysis of the cartridge.

6. A method according to claim 1, wherein the cartridge contains at least one sorbent matrix being permeable to and insoluble by the liquid, the matrix comprising a material having sorbent properties for components of the liquid being indicative for the chemical or biological properties thereof to be determined.

7. A device for being situated at a subsurface position of a liquid in order to determine chemical or biological properties of the liquid, the device comprising
    a casing having an inner fluid-filled cavity, the fluid having a density lower than the liquid,
    an inlet opening into the cavity provided with a backpressure regulating device so as to regulate liquid inflow rate into the cavity, said backpressure regulating device comprises a capillary tubing having an internal diameter of 10-500 µm, a cartridge arranged so that the inflow passes through the cartridge containing a material that interacts with components of the liquid so that said chemical or biological properties of the liquid may be determined by analysis of the cartridge, and an outlet opening for allowing a flow of the fluid out from the cavity, wherein the inlet opening of the sampling device is connected to a liquid conduit having its outlet inside the cavity above a bottom of the cavity, so that the free surface of the liquid inside the cavity during use of the device is below the liquid conduit outlet for the hydrostatic pressure driving the flow of the liquid into the cavity to be substantially constant.

8. A device according to claim 7, wherein the fluid in the cavity is a gas.

9. A device according to claim 7, wherein the liquid inflow rate at use of the device is within the range of 0.0001-5 Liters/day.

10. A device according to claim 7, wherein the volume inside the cavity below the level of the liquid conduit outlet and the liquid inflow rate allow for a sampling period of at least one hour before the free surface of the liquid inside the cavity will reach the level of the liquid conduit outlet.

11. A device according to claim 7, wherein the cartridge contains at least one sorbent matrix being permeable to and insoluble by the liquid, the matrix comprising a material having sorbent properties for components of the liquid being indicative for the chemical or biological properties thereof to be determined.

12. A device according to any one of claims 7 to 11, wherein the sorbent matrix comprises at least one of: silica, aluminium silicate, aluminium zirconium, metal oxides, synthetic ion exchange resins, carbonaceous materials, zeolites, carbohydrates and synthetic polymeric materials.

13. A device according to any one of claims 7 to 11, wherein the cartridge further comprises at least one fluid permeable partially soluble tracer material, which is released with controlled rate from the cartridge into fluids to be measured.

14. A device according to claim 13, wherein the at least one tracer material comprises at least one of: inorganic, organic and hybrid organic/inorganic salts; organic, inorganic or hybrid organic/inorganic solids, including polymers, copolymers, block copolymers and oligomers in which hydrolysis of certain bonds can lead to the loss of part of the material; and microencapsulated materials.

15. A device according to claim 14, wherein the tracer material is a salt having a solubility product in the fluid in question of between $10^{-2}$ and $10^{-60}$.

16. A device according to claim 14, wherein the tracer material is chosen from the following group of salts: $CaF_2$, Ca-Citrate, $CaHPO_4$, Ca-oleate and Ca-laurate.

17. A method for determining chemical or biological properties of a liquid, comprising:

situating a sampling device having a fluid-filled cavity at a subsurface position below an upper surface of the liquid, the fluid having a density lower than the liquid, allowing a flow of the liquid through an inlet opening of the sampling device said inlet opening is provided with a backpressure regulating device so as to regulate the liquid inflow rate into the cavity for a sampling period, said backpressure regulating device comprises a capillary tubing having an internal diameter of 10-500 µm, simultaneously allowing a flow of the fluid out from the cavity through an outlet opening of the sampling device, removing the sampling device from the subsurface position for subsequent analysis for determining said chemical or biological properties of the liquid, wherein the inflow passes through a cartridge containing at least one liquid permeable partially soluble tracer material, which is released with controlled rate from the cartridge into fluids to be measured, and a measure for the total liquid flow through the cartridge is obtained by analysing the remaining content of tracer material in the cartridge.

18. A method according to claim 17, wherein the at least one tracer material comprises at least one of: inorganic, organic and hybrid organic/inorganic salts; organic, inorganic or hybrid organic/inorganic solids, including polymers, copolymers, block copolymers and oligomers in which hydrolysis of certain bonds can lead to the loss of part of the material; and microencapsulated materials.

19. A method according to claim 18, wherein the tracer material is a salt having a solubility product in the fluid in question of between $10^{-2}$ and $10^{-60}$.

20. A method according to claim 18, wherein the tracer material comprises at least one of: $CaF_2$, Ca-Citrate, $CaHPO_4$, Ca-oleate and Ca-laurate.

21. A method according to claim 17, wherein the cartridge further contains a material that interacts with components of the liquid, and said chemical or biological properties of the liquid are determined by analysis of the cartridge.

22. A method according to claim 21, wherein said material comprises at least one sorbent matrix being permeable to and insoluble by the liquid, the matrix comprising a material having sorbent properties for components of the liquid being indicative for the chemical or biological properties thereof to be determined.

23. A method according to claim 17, wherein the inlet opening of the sampling device is connected to a liquid conduit having its outlet inside the cavity above the bottom of the cavity, so that the free surface of the liquid inside the cavity during most of the sampling period is below the liquid conduit outlet for the hydrostatic pressure driving the flow of the liquid into the cavity to be substantially constant during most of the sampling period.

24. A method according to claim 17, wherein the fluid in the cavity is a gas.

25. A method according to any one of claims 17 to 24, wherein said sampling period is at least one hour, preferably within the range of 1 days to 400 days and more preferred within the range of 14 days to 200 days.

26. A method according to claim 17, wherein the liquid inflow rate is within the range of 0.0001-5 Liters/day.

27. A device for being situated at a subsurface position of a liquid in order to determine chemical or biological properties of the liquid, the device comprising a casing having an inner fluid-filled cavity, the fluid having a density lower than the liquid, an inlet opening into the cavity provided with a backpressure regulating device so as to regulate the liquid inflow rate into the cavity, said backpressure regulating device comprises a capillary tubing having an internal diameter of 10-500 µm, and an outlet opening for allowing a flow of the fluid out from the cavity, wherein a cartridge is arranged so that the inflow passes through the cartridge containing at least one fluid permeable partially soluble tracer material, which is released with controlled rate from the cartridge into fluids to be measured.

28. A device according to claim 27, wherein the tracer material comprises at least one of: $CaF_2$, Ca-Citrate, $CaHPO_4$, Ca-oleate and Ca-laurate.

29. A device according to claim 27, wherein the inlet opening of the sampling device is connected to a liquid conduit having its outlet inside the cavity above the bottom of the cavity, so that the free surface of the liquid inside the cavity during use of the device is below the liquid conduit outlet for the hydrostatic pressure driving the flow of the liquid into the cavity to be substantially constant.

30. A device according to claim 27, wherein the liquid inflow rate at use of the device is within the range of 0.0001-1 Liters/day.

31. A device according to claim 27, wherein a volume inside the cavity below the level of the liquid conduit outlet and the liquid inflow rate allow for a sampling period of at least one hour, preferably within the range of 1 days to 400 days before the free surface of the liquid inside the cavity will reach the level of the liquid conduit outlet.

32. A device according to claim 27, wherein the fluid in the cavity is a gas.

33. A device according to claim 27, wherein the at least one tracer material comprises at least one of: inorganic, organic and hybrid organic/inorganic salts; organic, inorganic or hybrid organic/inorganic solids, including polymers, copolymers, block copolymers and oligomers in which hydrolysis of certain bonds can lead to the loss of part of the material; and microencapsulated materials.

34. A device according to claim 33, wherein the tracer material is a salt having a solubility product in the fluid in question of between $10^{-2}$ and $10^{-60}$.

35. A device according to claim 27, wherein the cartridge further comprises a material that interacts with components of the liquid so that said chemical or biological properties of the liquid may be determined by analysis of the cartridge.

36. A device according to claim 35, wherein said material contains at least one sorbent matrix being permeable to and insoluble by the liquid, the matrix comprising a material having sorbent properties for components of the liquid being indicative for the chemical or biological properties thereof to be determined.

37. A device according to claim 36, wherein the sorbent matrix comprises at least one of: silica, aluminium silicate, aluminium zirconium, metal oxides, synthetic ion exchange resins, carbonaceous materials, zeolites, carbohydrates and synthetic polymeric materials.

\* \* \* \* \*